United States Patent
Tornay et al.

(10) Patent No.: US 9,400,275 B2
(45) Date of Patent: *Jul. 26, 2016

(54) METHOD FOR PRODUCING MICROCARRIERS AND FOR PERFORMING BIOLOGICAL ASSAYS

(71) Applicant: MYCARTIS NV, Zwijnaarde / Ghent (BE)

(72) Inventors: Raphael Tornay, Illarsaz (CH); Nicolas Demierre, Chatel-St-Denis (CH); Stephan Gamper, Lausanne (CH); Philippe Renaud, Lausanne (CH)

(73) Assignee: MYCARTIS NV, Zwijnaarde/Ghent (BE)

( * ) Notice: Subject to any disclaimer, the term of this patent is extended or adjusted under 35 U.S.C. 154(b) by 0 days.

This patent is subject to a terminal disclaimer.

(21) Appl. No.: 14/414,905

(22) PCT Filed: Jul. 23, 2013

(86) PCT No.: PCT/EP2013/065544
§ 371 (c)(1),
(2) Date: Jan. 15, 2015

(87) PCT Pub. No.: WO2014/016309
PCT Pub. Date: Jan. 30, 2014

(65) Prior Publication Data
US 2015/0153333 A1   Jun. 4, 2015

(30) Foreign Application Priority Data
Jul. 24, 2012   (EP) ..................................... 12177717

(51) Int. Cl.
*G01N 33/53* (2006.01)
*B01L 3/00* (2006.01)
*G01N 33/543* (2006.01)
*C23F 1/02* (2006.01)

(52) U.S. Cl.
CPC ...... *G01N 33/5306* (2013.01); *B01L 3/502707* (2013.01); *B01L 3/502761* (2013.01);
(Continued)

(58) Field of Classification Search
CPC ................ B01L 13/502707; B01L 13/502761; B01L 13/545; C23F 1/02
See application file for complete search history.

(56) References Cited

U.S. PATENT DOCUMENTS

| 2001/0041369 A1 | 11/2001 | Chang et al. ................... 436/518 |
| 2005/0244955 A1 | 11/2005 | Li et al. ....................... 435/287.2 |

(Continued)

FOREIGN PATENT DOCUMENTS

| GB | 2 427 022 | 12/2006 | ............... G02B 5/18 |
| WO | WO 00/63695 | 10/2000 | ........... G01N 33/532 |

(Continued)

OTHER PUBLICATIONS

International Search Report for International Application No. PCT/EP2013/065544, Oct. 17, 2013.

(Continued)

*Primary Examiner* — Duy Deo
(74) *Attorney, Agent, or Firm* — Kusner & Jaffe

(57) ABSTRACT

The method according to the invention consists in providing a wafer having a bottom layer, a top first sacrificial layer and an insulating layer, structuring the first sacrificial layer to form a three dimensional structure onto which a first structural layer is deposited to define a corresponding three dimensional structure on the bottom surface of the first structural layer. The method consists also in forming a second three dimensional structure on the upper surface of the first structural layer.

15 Claims, 6 Drawing Sheets

(52) U.S. Cl.
CPC . *B01L3/545* (2013.01); *C23F 1/02* (2013.01); *G01N 33/54373* (2013.01); *B01L 2200/0647* (2013.01); *B01L 2200/10* (2013.01); *B01L 2200/12* (2013.01); *B01L 2300/0803* (2013.01); *B01L 2300/0819* (2013.01); *B01L 2300/0893* (2013.01)

(56) References Cited

U.S. PATENT DOCUMENTS

| | | | |
|---|---|---|---|
| 2010/0246005 A1 | 9/2010 | Moon et al. | 359/569 |
| 2011/0306506 A1* | 12/2011 | Demierre | B01L 3/502761 506/7 |
| 2014/0323330 A1* | 10/2014 | Bergo | G01N 33/54306 506/9 |
| 2015/0162141 A1* | 6/2015 | Tornay | B01L 3/502707 216/2 |
| 2015/0190803 A1* | 7/2015 | Demierre | B01L 3/502707 506/39 |

FOREIGN PATENT DOCUMENTS

| | | | |
|---|---|---|---|
| WO | WO 2010/072011 | 7/2010 | B01L 3/00 |
| WO | WO 2012/106827 | 8/2012 | B01L 3/00 |

OTHER PUBLICATIONS

Bhardwaj et al., "Advanced silicon etching using high density plasmas," SPIE vol. 2639, 224 (1995).

Schilp et al., "Advanced Etch Tool for High Etch Rate Deep Reactive Ion Etching in Silicon Micromachining Production Environment," Proceeding MST 2001.

Madou, 2002, "Deep Reactive Ion Etching (DRIE)," Fundamentals of Microfabrication, CRC Press, pp. 105-106.

* cited by examiner

METHOD FOR PRODUCING MICROCARRIERS AND FOR PERFORMING BIOLOGICAL ASSAYS

FIELD OF THE INVENTION

The invention relates to a microcarrier and to a method for producing microcarriers. The invention concerns in particular microcarriers suitable for performing a biological and/or a chemical assay for research and clinical laboratories.

BACKGROUND OF THE INVENTION

Within the scope of the present invention, a microcarrier or a microparticle refers to any type of microcarriers, respectively to any type of particles, microscopic in size, typically with the largest dimension being from 100 nm to 300 µm, preferably from 1 µm to 200 µm.

According to the present invention, the term microcarrier refers to a microparticle functionalized, or adapted to be functionalized, that is containing, or adapted to contain, one or more ligands or functional units bound to the surface of the microcarrier or impregnated in its bulk. A large spectrum of chemical and biological molecules may be attached as ligands to a microcarrier. A microcarrier can have multiple functions and/or ligands. As used herein, the term functional unit is meant to define any species that modifies, attaches to, appends from, coats or is covalently or non-covalently bound to the surface of said microcarrier or impregnated in its bulk. These functions include all functions that are routinely used in high-throughput screening technology and diagnostics.

Drug discovery or screening and DNA sequencing commonly involve performing assays on very large numbers of compounds or molecules. These assays typically include, for instance, screening chemical libraries for compounds of interest or particular target molecules, or testing for chemical and biological interactions of interest between molecules. Those assays often require carrying out thousands of individual chemical and/or biological reactions.

Numerous practical problems arise from the handling of such a large number of individual reactions. The most significant problem is probably the necessity to label and track each individual reaction.

One conventional method of tracking the identity of the reactions is achieved by physically separating each reaction in a microtiter plate (microarray). The use of microtiter plates, however, carries several disadvantages like, in particular, a physical limitation to the size of microtiter plates used, and thus to the number of different reactions that may be carried out on the plates.

In light of the limitations in their use, the microarrays are nowadays advantageously replaced by functionalized encoded microparticles to perform chemical and/or biological assays. Each functionalized encoded microparticle is provided with a code that uniquely identifies the particular ligand(s) bound to its surface. The use of such functionalized encoded microparticles allows for random processing, which means that thousands of uniquely functionalized encoded microparticles may all be mixed and subjected to an assay simultaneously. Examples of functionalized encoded microparticles are described in the international patent application WO 00/63695 and are illustrated in FIG. 1.

The international patent application WO 2010/072011 describes an assay device having at least a microfluidic channel which serves as a reaction chamber in which a plurality of functionalized encoded microparticles or microcarriers 1 (FIG. 1) can be packed. The microfluidic channel is provided with stopping means acting as filters that allow a liquid solution containing chemical and/or biological reagents to flow through while blocking the microcarriers 1 inside. The geometrical height of said microfluidic channels and the dimensions of said microcarriers 1 are chosen so that said microcarriers 1 are typically arranged in a monolayer arrangement inside each microfluidic channel preventing said microcarriers 1 to overlap each other.

Those functionalized encoded microcarriers 1 that show a favorable reaction of interest between their attached ligand(s) and the chemical and/or biological reagents flowing through may then have their code read, thereby leading to the identity of the ligand that produced the favorable reaction.

The code may comprise a distinctive pattern including a plurality of traversing holes 2 and an asymmetric orientation mark such as, for example, a L-shaped sign 3 (as shown in FIG. 1) or a triangle. This asymmetric orientation mark allows the distinction between the top surface 4 and the bottom surface 5 of the microcarrier 1.

The term microfluidic channel refers to a closed channel, i.e. an elongated passage for fluids, with a cross-section microscopic in size, i.e. with the smallest dimension of the cross-section being typically from about 1 to about 500 micrometers, preferably about 10 to about 200 micrometers. A microfluidic channel has a longitudinal direction, that is not necessarily a straight line, and that corresponds to the direction in which fluids are flowing within the microfluidic channel, i.e. preferably essentially to the direction corresponding to the average speed vector of the fluid, assuming a laminar flow regime.

With the assay device described in WO 2010/072011, the detection of a reaction of interest can be based on continuous readout of the fluorescence intensity of each encoded microcarrier 1 present in a microfluidic channel. In other words, the presence of a target molecule in the assay will trigger a predetermined fluorescent signal.

However, the functionalized encoded microparticles 1 and the assay device described in WO 2010/072011 do not allow for rapid quantification of reagent or ligand before an equilibrium state is reached, when the fluorescent signals saturate. Although the assay device of WO 2010/072011 decreases the time needed to reach equilibrium, in typical concentration values of analyte in the nano-molar range, ten to twenty minutes are still required, while lower concentration in the pico-molar range can take up to hours to be reached and serve for quantification. Moreover, the discrepancies in their fluorescent signals, in particular the diffusion pattern even after the end of the assay do not determine a quantitative information with a lower margin of error than about 15%.

To remedy these drawbacks, the patent application PCT/CH2012/000032 proposes an encoded microcarrier, shown in FIGS. 2 and 3, comprising a body 6 having a shape of a right circular cylinder and comprising a top surface 4, a bottom surface 5 and spacing elements 7 protruding from the bottom surface 5.

The microcarrier 1 with its spacing elements 7 is shaped to ensure that, when the encoded microcarrier 1 is laid on a flat plane 8 with the detection surface 5 facing said plane 8, a gap d exists between said flat plane 8 and the detection surface 5, as shown in FIG. 3.

As said above, the encoded microcarrier contains one or more ligands bound to the bottom surface 5 (detection surface). When contacting the ligand-bound encoded microcarrier 1 with a solution that may contain one or more target analytes, a reaction of interest may occur on the detection surface 5, depending on the presence or absence of a proper analyte. As an example, a reaction of interest can emit or inhibit a fluorescent signal, which can be monitored. Detecting a reaction on the detection surface 5 can allow determining the presence or absence of particular analytes of interest.

The document PCT/CH2012/000032 also discloses an assay system comprising a plurality of encoded microcarriers 1 with spacing elements and an assay device, partially shown in FIGS. 4 and 5. The assay device 9 has at least one microfluidic channel 10 having an inlet connected to an inlet well 11 and an outlet connected to an outlet well 12, said channel 10 being shaped to accommodate a plurality of said encoded microcarriers 1. The microfluidic channel 10 is provided with stopping means 13 arranged in the vicinity of the outlet of the microfluidic channel 10 and acting as a filter that allow a liquid solution to flow through while blocking said encoded microcarriers 1 inside. The microfluidic channel 10 has a cross-section that allows at least two encoded microcarriers 1 to be arranged side by side over the length of said microfluidic channel 10, in a monolayer arrangement as depicted in FIG. 5. The microfluidic channel 10 comprises at least an observation wall 14 through which an assay is monitorable. Typically, when the assay is monitored by fluorescent signal, the observation wall is transparent.

In such an assay system, when the encoded microcarriers are loaded in the microfluidic channel 10 with said detection surface 5 facing said observation wall 14, the spacing elements 7 generate a gap d between said detection surface 5 and said observation wall 14 to allow a circulation of liquid in said gap d, said liquid containing chemical and/or biological reagent of interest for the assay.

Thus, the spacing elements 7 permit a more homogeneous convective flow all over the microfluidic channel 10 resulting in homogeneous fluorescent increase over time and across encoded microcarriers 1. The homogeneous signal increase allows for a rapid quantification of the analyte being flushed, from the first seconds, by monitoring the fluorescence rate.

When microcarriers 1 are introduced into the inlet well 11, said microcarriers 1 may flip over during their sedimentation in the well 11. Thus, some of the microcarriers 1 have their detection surface 5 opposite to the detection wall 14 of the microchannel 10. However, the detection of the presence of molecules bound to the detection surface 5 is possible only when said surface 5 is facing the detection wall 11. Thus, microcarriers 1 having a wrong orientation do not emit any detectable signal.

Moreover, the laminar fluid flow is disturbed by the microcarriers 1 which are not properly oriented. Indeed, in this case, said laminar fluid flow is forced to move around the concerned microcarriers 1, thus creating a velocity field of the fluid flow that is inhomogeneous in the microfluidic channel 10 leading to an inhomogeneous distribution of the reagents and target molecules intended to interact with the detection surfaces 5. This affects the reliability of the assay.

More generally, the same orientation problem could arise with other kind of microcarriers having only one of the bottom and top surfaces provided with a three-dimensional structure.

SUMMARY OF THE INVENTION

The present invention aims to remedy all or part of the disadvantages mentioned above.

To this aim, the invention proposes a method for producing at least a microcarrier, the method comprising the following steps:

a) providing a wafer having a sandwich structure comprising a bottom layer, a top first sacrificial layer and an insulating layer located between said bottom and top layers;

b) structuring the first sacrificial layer to form a first mask delineating a first three dimensional negative pattern;

c) depositing a first structural layer over the first sacrificial layer so as to form a first three dimensional structure complementary to the first three dimensional negative pattern;

d) depositing a second sacrificial layer over the top surface of the first structural layer;

e) structuring the second sacrificial layer to define a second mask delineating a second three dimensional negative pattern on the top surface of the first structural layer;

f) depositing a second structural layer in the second three dimensional negative pattern so as to form a second three dimensional structure on the upper surface of the first structural layer;

g) etching away from above the first and second structural layers down to the insulating layer to delineate lateral walls of bodies of microcarriers, each body comprising at least a first lower and a second upper three dimensional structures;

h) etching away the insulating layer, the bottom layer and the sacrificial layers to release the microcarriers.

The microcarriers obtained by the method according to the invention comprise three-dimensional structures on both top and bottom surfaces. Thus, when these microcarriers are used in the above mentioned microchannel, the formation of a perturbed fluid flow during a biological and/or chemical assay is prevented and a laminar fluid flow is maintained throughout the microchannel, whatever the orientation of the microcarriers in the microchannel.

The method according to the invention allows microcarriers to be obtained by successively stacked and structured layers onto an initial wafer.

According to an embodiment of the method of the present invention, the first and/or the second three-dimensional structure comprise at least one spacing element protruding from the corresponding surface of the body of the onto which they are formed.

Said spacing element provides a gap between the corresponding surface of the microcarrier and the surface on which said microcarrier rests, in order to create a laminar fluid flow through said microchannel.

The method may comprise, before step c, a step of depositing a first active layer on the first sacrificial layer and onto the first three dimensional negative pattern.

The method may also comprise, before step g, two additional steps consisting in:

a) etching away the second sacrificial layer; and b) depositing a second active layer over the first and second structural layers.

For example, the first active layer and/or the second active layer comprise a material having optical or magnetic properties, polycrystalline silicon and/or polytetrafluoroethylene, or a metallic layer having a high reflective index.

Using a material having optical properties will increase substantially the fluorescent signal emitted from the corresponding surface of the microcarrier. A material having magnetic properties can be used to orientate the microcarrier in a desired direction, for example. The use of polycrystalline silicon increases the roughness of the corresponding surface of the body in order to increase the effective area to be coated on said surface. Finally, polytetrafluoroethylene can be used to reduce the friction between the microcarrier and the surface on which it rests during the assay.

The first active layer and/or the second active layer may comprise an oxide or a nitride, for example silicon dioxide, or a metal layer. Thus the signal emitted by the molecules bound to said surface is enhanced.

According to another embodiment of the invention, the three-dimensional structure of the top surface and/or the three-dimensional structure of the bottom surface comprise at least one diffraction grating.

The diffraction grating refers to a structure designed to split and diffracts light into several beams travelling in different directions. The diffraction grating generates a surface plasmon resonance (and thus a detectable signal) on the top surface and/or on the bottom surface of the microcarrier when illuminated by light. Moreover, the diffraction grating is intended to interact with target molecules inducing variations of the surface plasmon resonance. These variations can be detected to determine the presence or the absence of said target molecules. The document GB2427022 discloses a microcarrier having only one surface comprising a diffraction grating.

In a particular embodiment, the method further comprise a step consisting in polishing the upper surface of the first continuous layer so as to form a flat upper surface, before step d.

In one possible embodiment of the invention, the insulating layer and the first sacrificial layer form a single layer such as a single layer comprising silicon nitride.

At least one of the sacrificial layers may be made of or may comprise silicon nitride or photoresist material.

Advantageously, the continuous layer is made of or comprises silicon, preferably amorphous silicon or polysilicon.

The invention also relates to a microcarrier obtained by the method according to the invention, the microcarrier comprising a body having a top surface and a bottom surface, each of said surfaces comprising a three-dimensional structure.

BRIEF DESCRIPTION OF THE DRAWINGS

The invention can be better understood and other details, features, and advantages of the invention appear on reading the following description made by way of non-limiting examples with reference to the accompanying drawings, in which.

DETAILED DESCRIPTION OF THE INVENTION

A method for producing microcarriers according to the invention will be described with reference to FIGS. 6 to 18. This method comprises the following successive steps.

Figure 6:
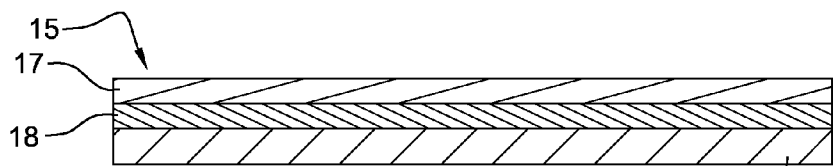
FIGS. 6 to 17 illustrate the successive steps of the method for producing microcarriers according to an embodiment the invention.

A first step, shown in FIG. 6, consists in providing a wafer 15 having a sandwich structure, which comprises a bottom layer 16, a top first sacrificial layer 17 and an insulating layer 18 located between said bottom and top layers 16, 17.

For example, the bottom layer 16 is made of silicon material. The insulator layer 18 may be made of material capable of spatially isolating two silicon layers chosen amongst, silicon nitride, tungsten, chromium or aluminum each of them acting as an insulator for the bottom layer. The top first sacrificial layer 17 may be made of silicon nitride deposited on the insulator layer 18 by a low pressure chemical vapor deposition (LPCVD) method or by a sputtering method.

The method according to the invention further comprises a step of structuring the top first sacrificial layer 17 to define a three-dimensional structure on the insulating layer 18.

To this aim, a second step consists in applying a photosensitive resist layer 19 (FIG. 7) onto the top first sacrificial layer 17. In order to delineate the three-dimensional structure, the photosensitive resist layer 19 is illuminated with UV light through a mask (not shown), such as a chrome/glass mask. Open patterns in the mask corresponding to the three-dimensional structure layout provide a space-selective UV illumination. Photo initiators react and start polymerizing the resist layer where the resist has been space-selectively illuminated. Specific chemistry is then used to remove unexposed and unreacted parts of the photosensitive resist layer. The remaining pattern of the hardened resist layer 19 defines the shape of spacing elements 20.

The photosensitive resist 19 may be positive or negative photoresist. One example for a positive resist is MICROPOSIT S 1805 PHOTO RESIST supplied by Shipley Company and one example for a negative photoresist is GM1040 SU-8 PHOTO EPOXY as supplied by Gersteltec Engineering Solutions. The photosensitive resist layer may be applied onto the wafer by different techniques known in the art, such as spray coating, or preferably spin coating.

Figure 7:
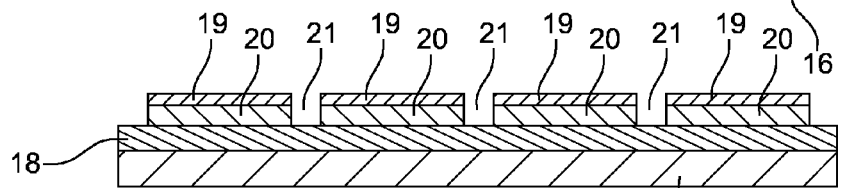

Then, as shown in FIG. 7, a third step consists in etching the first sacrificial layer 17 over its entire height to delineate spacing elements 20 protruding upward. This may be done by deep reactive silicon etching (DRIE) or wet etch.

In a possible embodiment of the invention, the etching step may be made on a part of the height only of the first sacrificial layer 17.

Figure 8:
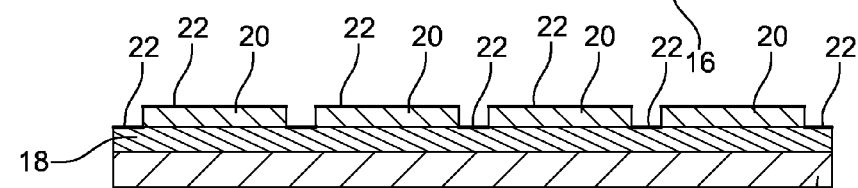

In a fourth step, shown in FIG. 8, the photosensitive resist 19 is removed in a wet chemical bath. Thus, it remains a clean monocristalline silicon layer defining a series of spacing elements 20 defining a first three dimensional structure delineating a first three dimensional negative pattern formed with recesses 21.

A fifth step, shown in FIG. 8, consists in depositing a first active layer 22 on the top surfaces 4 of the protruding elements 20 and in recesses 21 defining the first three dimensional negative pattern.

The first active layer 22 is a layer having optical properties, such as an oxide layer comprising silicon dioxide. The thickness of the first layer 22 is approximately between 90 and 120 nm when working with red fluorescence labels. Any other dielectric material, such as a nitride could also be used. Optionally, the dielectric material can be also combined with a metal layer.

Different types of oxide deposition methods can be used such as PECVD (Plasma-enhanced chemical vapor deposition), evaporation, or sputtering (Madou M J, 2002, Fundamentals of microfabrication, CRC Press). For the deposition of silicon dioxide from PECVD technique, a mixture of gases such as dichlorosilane or silane and oxygen may be used, typically at pressures from a few hundred milliTorr to a few Torr. The deposition of the silicon dioxide is performed with a temperature comprised in a range from room temperature to 300° C.

Figure 9:
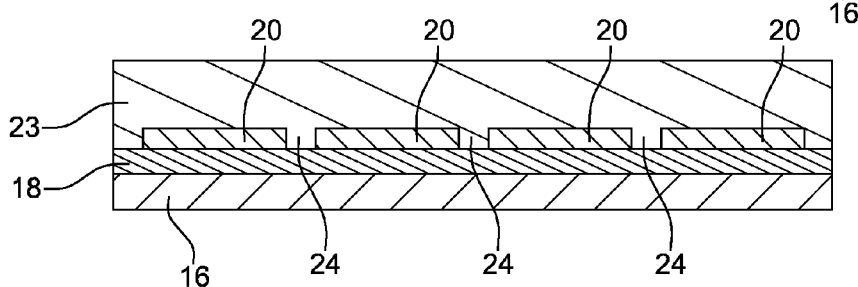

A sixth step, shown in FIG. 9, consists in depositing a first structural layer 23 over the three dimensional structure 20 and the recesses forming the first three dimensional negative pattern so as to form a first complementary three dimensional structure 24 on the lower surface of the first structural layer 23.

The first structural layer 23 may be made of polysilicon or amorphous silicon and deposited using a LPCVD method or sputtering method.

Figure 10:
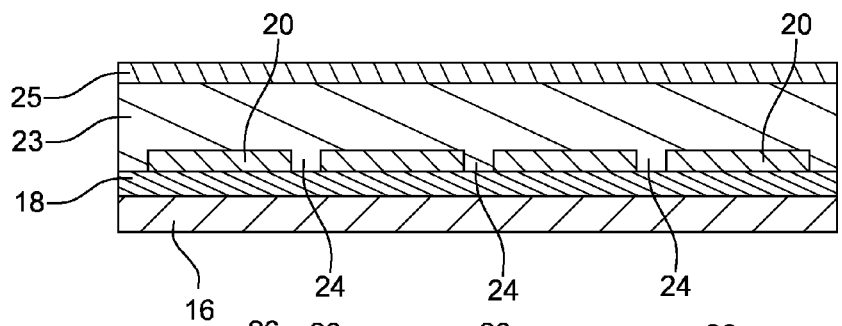

A seventh step, shown in FIG. 10 consists in depositing a second sacrificial layer 25 on the upper surface of the first structural layer 23. The second sacrificial layer 25 may be made of silicon nitride deposited for example by a LPCVD method.

An eighth step consists in applying another photosensitive resist layer 26 (FIG. 11) onto the second sacrificial layer. The photosensitive resist layer is illuminated with UV light through a mask (not shown), such as a chrome/glass mask. As previously, open patterns in the mask provide a space-selective UV illumination. Photo initiators react and start polymerizing the resist layer 26 where the resist has been space-selectively illuminated. Specific chemistry is then used to remove unexposed and unreacted resist. The remaining pattern of the hardened resist layer 26 defines the shape of spacing elements 27.

Figure 11:
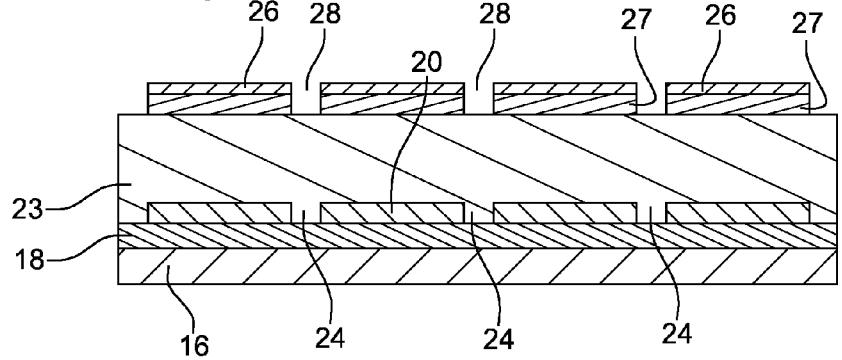

Then, as shown in FIG. 11, a ninth step consists in etching the second sacrificial layer over its entire height to delineate spacing elements 27 protruding upward. This may be done by deep reactive silicon etching (DRIE) or wet etch.

Figure 12:
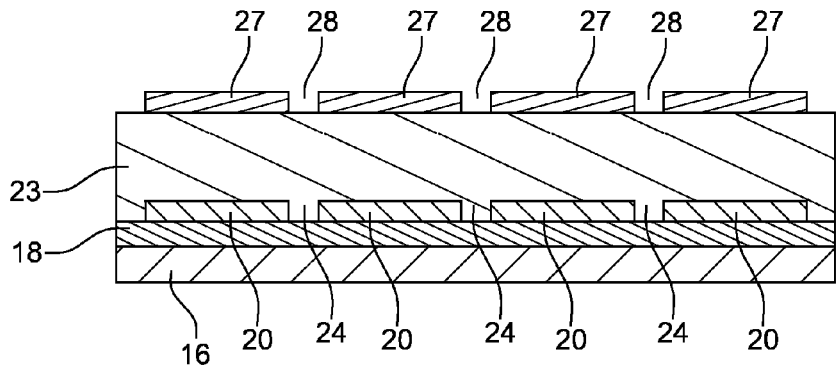

In a tenth step, shown in FIG. 12, the photosensitive resist 26 is removed in a wet chemical bath. Thus, it remains a clean silicon layer defining a series of spacing elements 27 defining a second three dimensional structure delineating a second three dimensional negative pattern formed with recesses 28.

Figure 13:
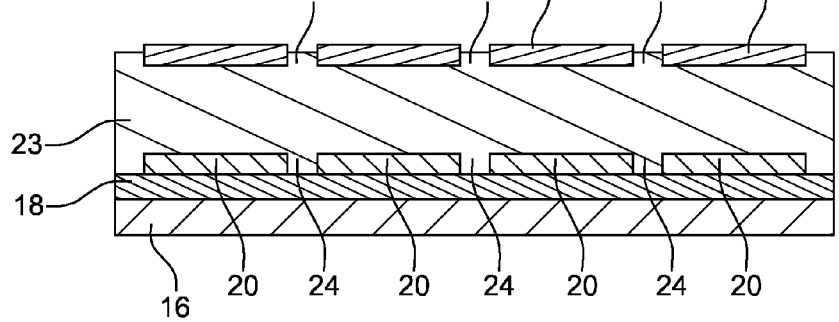

A eleventh step, shown in FIG. 13, consists in depositing a second structural layer 29 in the second three dimensional negative pattern onto the first structural layer 23 so as to form a second three dimensional structure on the upper surface of the first structural layer 23.

The second structural layer 29 may be made of polysilicon or amorphous silicon deposited by a process of Low Pressure Chemical Vapor Deposition (LPCVD).

Figure 14:
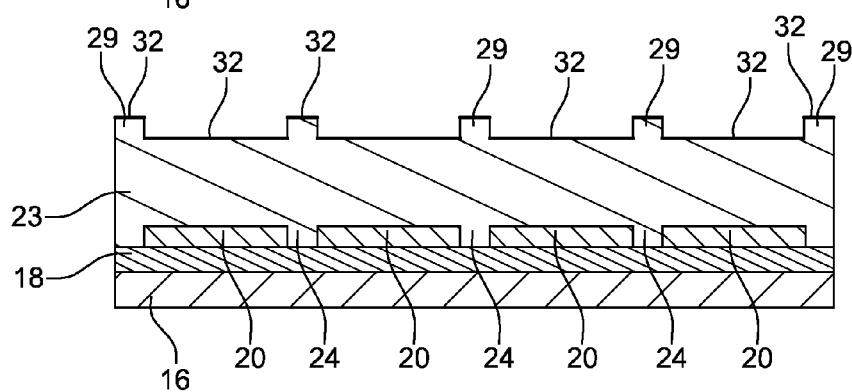

A twelfth step, shown in FIG. 14, consists in completely etching away the second sacrificial layer 27, i.e. the spacing elements 27 using dry etch or wet etch process.

In order to produce bi-layered microcarriers 1, the method according to the invention comprises an thirteenth step, shown in FIG. 14, which consists in depositing a second active layer 32 over the upper three dimensional structure 29 and in recesses delineated between the three dimensional structure 29. The second active layer 32 has also optical properties, such as an oxide layer comprising silicon dioxide. The thickness of the second active layer 27 is approximately between 90 and 120 nm when working with red fluorescence labels. Any other dielectric material (such as a nitride) or a metal layer could also be used.

The second active layer 32 may be deposited with the same method used for the deposition of the first active layer 22.

Figure 15:
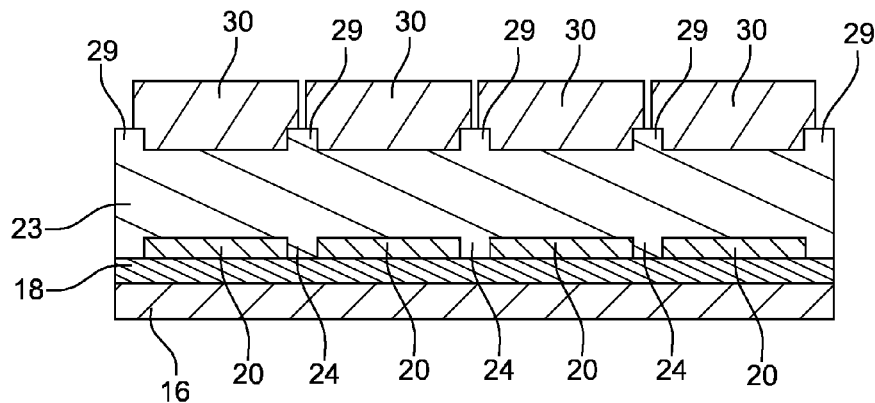
Figure 16:
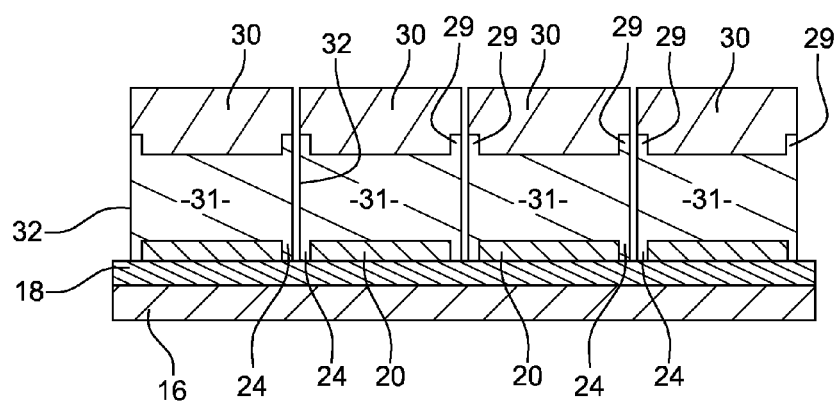
Figure 17:
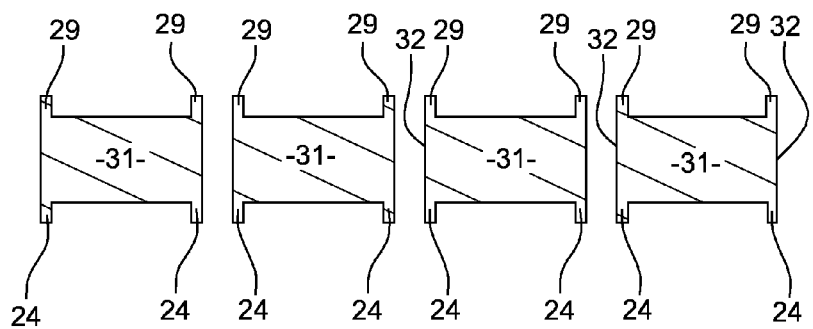

A fourteenth step, shown in FIG. 15, consists in forming a third sacrificial layer 30 onto the first and second structural layers. This third sacrificial layer forms a mask comprising openings allowing the first 23 and second 29 structural layers to be etched away from above down to the insulating layer as shown in FIG. 16, so as to delineate lateral walls 32 of individual microcarriers 31 (FIG. 17). To do so a photoresist is applied and patterned. Then etching is performed using dry etch, the Bosch Process and dry etch. The Bosch process is disclosed in the document "J. K. Bhardwaj, H. Ashraf, Proc. SPIE, 2639, 224 (1995); A. Schilp, M. Hausner, M. Puech, N. Launay, H. Karagoezoglu, F. Laermer, Advanced etch tool for high etch rate deep reactive ion etching in silicon micromachining production environment, Proceeding MST 2001, Dusseldorf". The Deep Reactive Ion Etching is disclosed in the document "Madou M J, 2002, Fundamentals of microfabrication, CRC Press".

After being delineated, the microcarriers are released by etching away the insulating layer 18, the first sacrificial layer 20 and the third sacrificial layer 30 remaining respectively on the lower and upper surfaces of bodies of microcarriers 31. Thus, the third sacrificial layer 30 and first sacrificial layer 20 are respectively removed by a wet etching and then by a Bomba-release process consisting in contacting the sacrificial layer with a phosphoric acid bath ($H_3PO_4$) heated to a temperature of 180° C.

The released microcarriers 1 may be kept in suspension in liquid containers or vessels until use in an assay.

Figure 18:
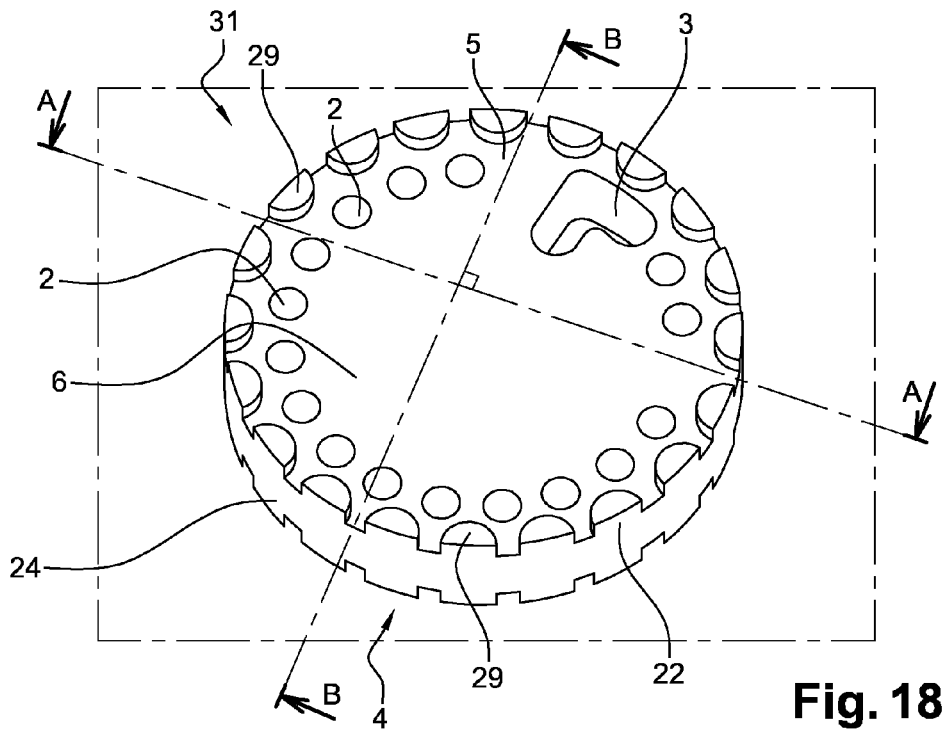
FIG. 18 illustrates a bottom perspective view of a microcarrier according to the invention.
Figure 19:
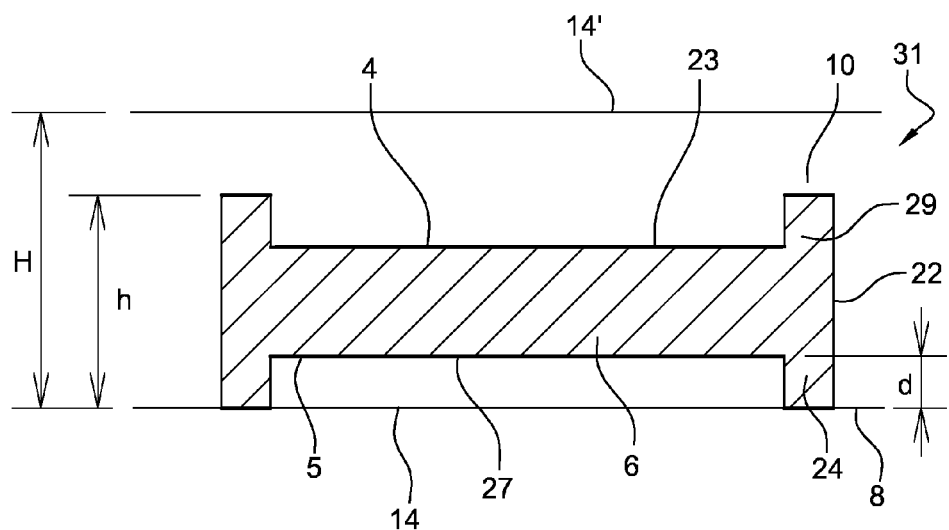
FIG. 19 illustrates a cross-section view of the microcarrier according to the invention in a microchannel.

FIGS. 18 and 19 illustrate a microcarrier 1 obtained by the above mentioned method and comprising a body 6 having a top surface 4 and a bottom surface 5. A first set of spacing elements 24 protrudes from the top surface 4 of the body 6. A second set of spacing elements 29 protrudes from the bottom surface 5 of the body 6. Each set comprises for example twenty spacing elements 24, 29.

Each spacing element 24, 29 has a shape of a truncated right cylinder, is disposed on the periphery of the corresponding surface 4, 5 and extends in the continuation of the cylindrical lateral wall 22 of the body 6. Each circular right cylinder is truncated along its height by the cylindrical wall 22 of the microcarrier 1.

Alternatively, each spacing element 24, 29 has a shape of a truncated cone or of a spike (not shown).

The surface of the spacing elements 24, 29 represents less than 20% of the corresponding surface 4, 5, preferably less than 15%.

The microcarrier 1 with its spacing elements 24, 29 is shaped to ensure that, when the microcarrier 1 is laid on a flat plane 14, a gap d exists between said flat plane 14 and the bottom or top surface 5, 4 of the body 6, as shown in FIG. 19.

Figure 5:
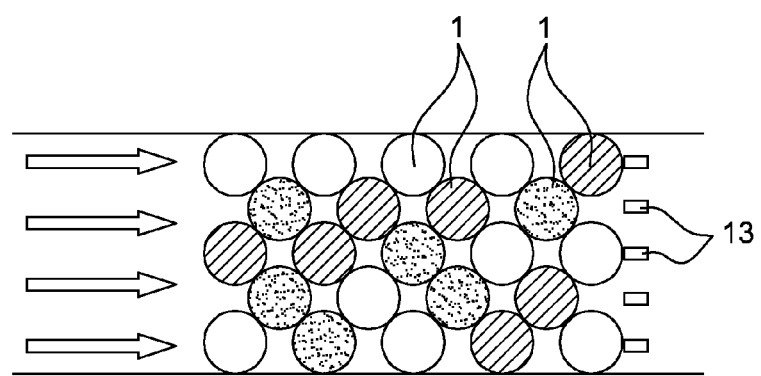
FIG. 5 illustrates a top view of encoded microcarriers loaded in the microfluidic channel of FIG. 4.

Advantageously, the height of the gap d is less than 30% of the greatest height h of the encoded microcarrier 1 (FIG. 5). Most preferably, the distance d is greater than 5% of the height h, more preferably 10%. In the example of the figures, the Height h of the encoded microcarrier 1 is about 10 μm and the distance d is about 1 μm.

The microcarrier 31 also comprises a code comprising a distinctive pattern made of a plurality of traversing holes 2 and an asymmetric orientation mark such as, for example, a L-shaped sign 3 (as shown in FIG. 18) or a triangle. This asymmetric orientation mark allows the distinction between the top surface 4 and the bottom surface 5 of the body 6 of the microcarrier 31.

Each surface 4, 5 of the body 6 is also covered with a homogeneous and continuous active layer 22, 32.

Each microcarrier 31 is preferably shaped in the form of a disk having a diameter between 1 and 200 μm, for example 40 μm.

Each surface 4, 5 further has an area wherein, when the encoded microcarrier 31 is laid on the flat plane 14, each point of said area belongs to the two different cross-sections along the axis AA and BB, shown in FIG. 18, which are perpendicular to each other and to said plane 14. Said cross-sections AA and BB are free of spacing element 24, 29. This ensures that, when the microcarrier 31 lays flat against said flat plane 14 and is in a laminar flow essentially parallel to that flat plane 14, the orientation of the microcarrier 31 around an axis normal to the flat plane does not significantly affect the flow in the gap d. In other words, there is no preferred rotational orientation of the microcarrier 31 with regard to the flow, which would change the efficacy of a reaction.

The microcarrier 31 is also functionalized, or is adapted to be functionalized. Thus, one or more ligands or functional units are bound to the surfaces 4, 5 of the microcarrier 1 or impregnated in its bulk.

Figure 1:
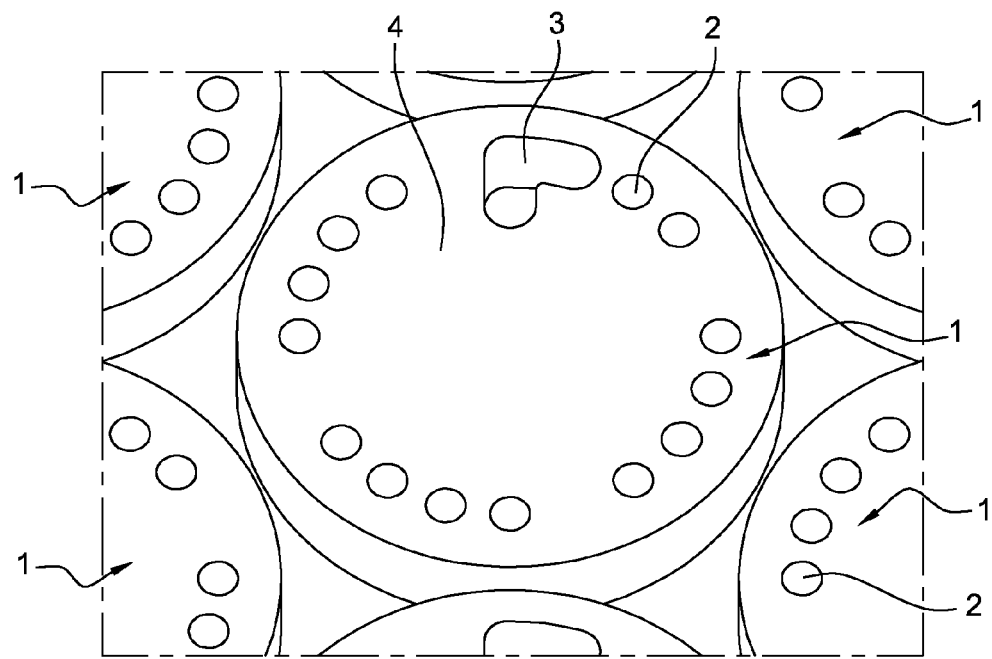
FIG. 1 illustrates a top perspective view of microcarriers according to the prior art.
Figure 2:
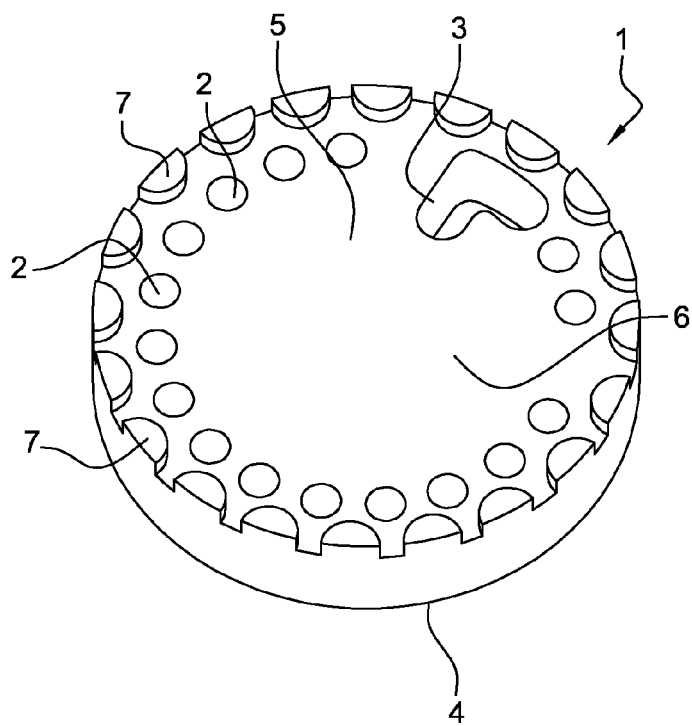
FIG. 2 illustrates a bottom perspective view of a microcarrier according to the prior art, having spacing elements protruding from a bottom surface of the microcarrier.
Figure 3:
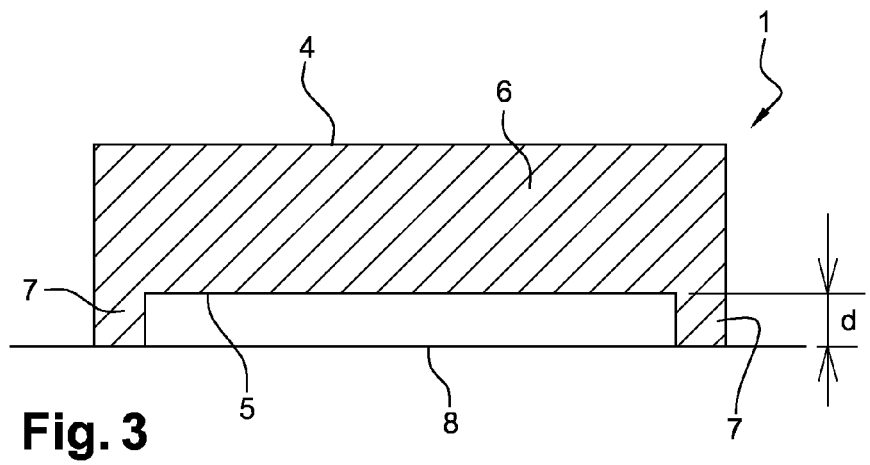
FIG. 3 illustrates a cross-section view of the microcarrier shown in FIG. 2.
Figure 4:
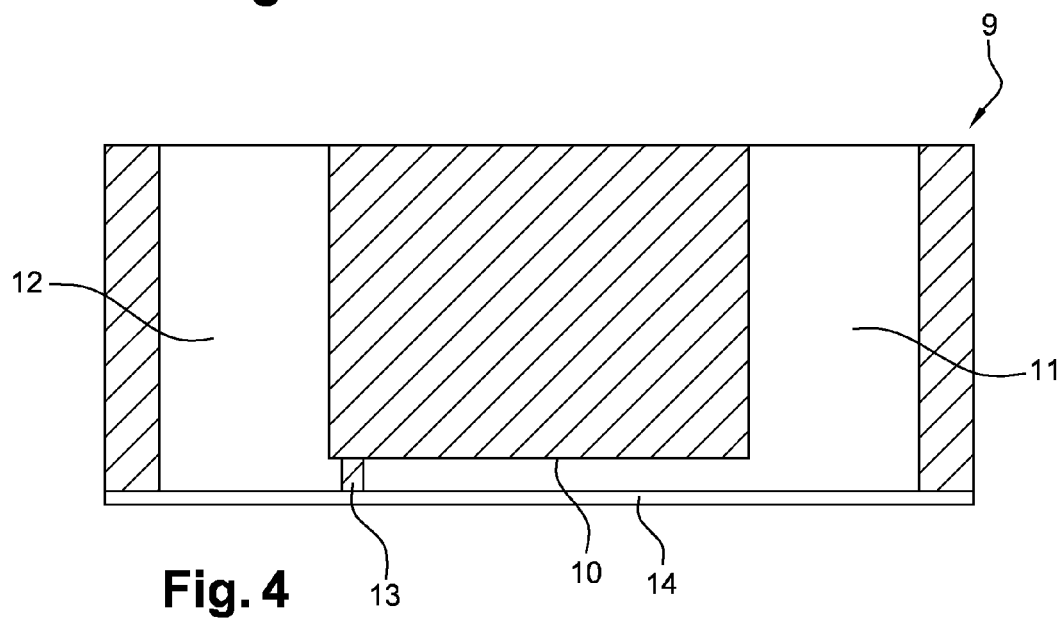
FIG. 4 illustrates a cross-section view of a microfluidic channel of an assay device according to the prior art.

When such microcarrier 31 is used in an assay device similar to the one shown on FIG. 4, whatever the orientation of the microcarrier 1 in the microchannel 10, a gap always exists between the bottom surface 5, respectively the top surface 4 of the body 6 of the microcarrier 31, and the bottom surface 14, respectively the top surface 14' of the microchannel 10.

In addition, whatever the orientation of the microcarrier 31 in the microchannel 10, a functionalized surface provided with an active layer is always facing the bottom surface 14 of the microchannel 10, i.e. the observation wall through which the assay is monitored. When the assay is monitored by fluorescent signal, the observation wall 14 is transparent.

The gaps permit a homogeneous convective flow all over the microfluidic channel 10 and all over the functionalized surfaces 4, 5 of the body 6, resulting in a homogeneous fluorescent increase over time. Therefore, the analyte being flushed can rapidly and reliably be quantified.

Other embodiments of the invention will be apparent to those skilled in the art from consideration of the specification and practice of the invention disclosed herein. It is intended that the specification and example be considered as exemplary only, with the true scope and spirit of the invention being indicated by the following claims.

Having described the invention, the following is claimed:

1. A method for producing at least a microcarrier, the method comprising the following steps:
    a) providing a wafer having a sandwich structure comprising a bottom layer, a top first sacrificial layer and an insulating layer located between said bottom and top layers;
    b) structuring the first sacrificial layer to form a first mask delineating a first three dimensional negative pattern;
    c) depositing a first structural layer over the first sacrificial layer so as to form a first three dimensional structure complementary to the first three dimensional negative pattern;
    d) depositing a second sacrificial layer over the top surface of the first structural layer;
    e) structuring the second sacrificial layer to define a second mask delineating a second three dimensional negative pattern on the top surface of the first structural layer;
    f) depositing a second structural layer in the second three dimensional negative pattern so as to form a second three dimensional structure on the upper surface of the first structural layer;
    g) etching away from above the first and second structural layers down to the insulating layer to delineate lateral walls of bodies of microcarriers, each body comprising at least a first lower and a second upper three dimensional structures; and
    h) etching away the insulating layer, the bottom layer and the sacrificial layers to release the microcarriers.

2. A method according to claim 1, wherein the first and/or the second three-dimensional structures comprise at least one spacing element protruding from the corresponding surface of the body onto which they are formed.

3. A method according to claim 1, further comprising, before step c, a step of depositing a first active layer on the first sacrificial layer and onto the first three dimensional negative pattern.

4. A method according to claim 1, further comprising the following steps, before step g:
    a) etching away the second sacrificial layer; and
    b) depositing a second active layer over the first and second structural layers.

5. A method according to claim 3, wherein at least one of the first active layer or the second active layer comprises a material having optical or magnetic properties, polycrystalline silicon and/or polytetrafluoroethylene, or a metallic layer having a high reflective index.

6. A method according to claim 5, wherein the first active layer and/or the second active layer comprise an oxide or a nitride, or a metal layer.

7. A method according to claim 1, wherein at least one of the first three dimensional structure and second three dimensional structure of each microcarrier comprises at least a diffraction grating.

8. A method according to claim 1, further comprising before step d, a step of polishing the upper surface of the first structural layer so as to form a flat upper surface.

9. A method according to claim 1, wherein the insulating layer and the first sacrificial layer form a single layer.

10. Method according to claim 1, wherein at least one of the sacrificial layers is made of or comprises silicon nitride or photoresist material.

11. A method according to claim 1, wherein the first and second structural layers comprise silicon.

12. A method according to claim 6, wherein said oxide is silicon dioxide.

13. A method according to claim 9, wherein said single layer comprises silicon nitride.

14. A method according to claim 11, wherein said silicon is amorphous silicon.

15. A method according to claim 11, wherein said silicon is polysilicon.

* * * * *